United States Patent [19]
Takasuka et al.

[11] Patent Number: 4,648,908
[45] Date of Patent: Mar. 10, 1987

[54] COATED PIGMENT AND COSMETIC MATERIALS COMPRISING THE SAME

[75] Inventors: Yutaka Takasuka, Kamakura; Kunihiko Mohri, Shizuoka; Akiko Kawaguchi, Shimizu, all of Japan

[73] Assignee: Pola Chemical Industries Inc., Japan

[21] Appl. No.: 632,334

[22] Filed: Jul. 19, 1984

[30] Foreign Application Priority Data

Feb. 28, 1984 [JP] Japan .................................. 59-36985

[51] Int. Cl.⁴ ........................ C04B 14/00; C09C 1/00; A61K 7/035
[52] U.S. Cl. .................................. 106/308 F; 424/69; 106/308 Q
[58] Field of Search ...................... 106/308 F, 308 G; 424/69

[56] References Cited

U.S. PATENT DOCUMENTS

| | | | |
|---|---|---|---|
| 3,656,982 | 4/1972 | Chapman | 106/291 |
| 4,128,630 | 12/1978 | Hayashi et al. | 424/69 |
| 4,148,667 | 4/1979 | Ziobrowski | 106/288 Q |
| 4,216,201 | 8/1980 | Calvo | 424/168 |

*Primary Examiner*—Theodore Morris

[57] ABSTRACT

Pigments coated with metallic soap and containing water easily disperse in the water and yet demonstrate water-repellency. The present pigments will thus obtain cosmetic which will give the user a refreshment and longer lasting and water-repellent make-up.

11 Claims, 1 Drawing Figure

COATED PIGMENT AND COSMETIC MATERIALS COMPRISING THE SAME

BACKGROUND OF THE INVENTION

1. Field of the Invention

The present invention relates to a novel coated pigment, and more particularly it relates to a coated novel pigment applicable to various products such as cosmetics and paints which is easily dispersed in water and is water-repellent when water in the mixture has been evaporated after dispersion, and cosmetic materials comprising said pigments.

2. Description of the Prior Art

Generally, various products containing pigments such as cosmetic and paint materials are roughly classified into aqueous non-aqueous, emulsion and powder types, and such products contain coated pigments which are selected according to the property of the medium used or the method of dispersing the pigment. Aqueous products, in particular, employ pigments coated with aqueous dispersant such as phosphoric acid, or pigments coated with silica in order to facilitate dispersion of pigments in the product. For practical purposes, however, aqueous products are also expected to exhibit the water-repellency after application. This is to prevent the applied product from being washed away from the surface by water or perspiration. Oil drops are often dispersed in an aqueous phase to obtain an emulsion so that the aqueous products may also be provided with water-repellent property. With aqueous products containing a large amount of said pigment coated with aqueous dispersant, addition of such oily drops will not give the products water-repellency or lipophilic property. In order to make aqueous products such as a cosmetic foundation containing a large amount of pigment lipophilic on the skin, it is necessary to make the pigment itself lipophilic. However, the present situation in the art is such that no pigments which are lipophilic in the aqueous system are available.

Aqueous cosmetics presently available on the market such as foundations, eye-liners, or eye-colors, give refreshment when applied on the skin. However, they are easily affected by perspiration, tear drops, water, sebum, etc., and since these products are not water-repellent, the make-up comes off easily and does not last. These products are further defective in that the make-up will become easily washed while swimming or in the rain because of lack of water-resistance. On the other hand, with non-aqueous phase especially oil-phase products, they feel soft and moist on the skin because the vehicle itself is oil. But the feel is also oily and sticky at the time of application. They also tend to "gather" because of sebum and the make-up is likely to come off. The demand, therefore, has been for a novel product which combines the advantages of aqueous and non-aqueous phases to overcome the respective defects mentioned above.

Conventional stick-type cosmetics, on the other hand, are generally made of so-called oil gels formed into sticks. They are either formed by extrusion using an oily substance such as oil, fat, wax, hydrocarbons, etc. as the binder or the structural component with an addition of a pulverulent body, or by casting fluid materials at a high temperature. Such oil gel stick cosmetics are typically and widely used in various products such as lipsticks, eye-shadows, eye-brow pencils, eye-liners, rouges, etc. These cosmetics come in various forms such as pencils or in a roll-up container, and are advantageous in that they can be directly applied to the skin, portable and handy in use and feel smooth on the skin. On the other hand, they are defective in that they are oily, come off easily, or give different feelings depending on the temperature at the time of use. All those merits and demerits of the conventional stick-type cosmetics arise from the limitations in mix ratio of powder, oily substance and wax. Since the ratio cannot be radically changed because of restrictions in manufacture and the quality requirements of the product, these merits and demerits have become inherent part of the essential properties of stick cosmetics. And yet, improvements on these points have been urgently felt. For example, the properties of cosmetics may differ depending on the ratio of powder to oily and wax such that when the base compound contains less than 50% of powder (oily range), it will give the feeling of oiliness; with more than 80% of powder (powdery range), it will give the feeling of powderiness; with 80 to 50% of powder (medium range) the base compound will give different feelings depending on the properties of individual component materials. Most of the conventional stick cosmetics are the oily type, because with a greater content of powder, operations such as kneading, filling and molding become more difficult. These conventional products generally contain from several to 40% of powder depending on the purpose, and thus inevitably entail the above demerits mentioned of oily cosmetics. Whereas if the powder content is greater, the tip of the stick where it directly touches the skin will become hardened as it wears by repeated use (caking), so much so that eventually it becomes unusable. This caking is a phenomenon of hardening of stick-type cosmetics caused by adhesion or permeation of sebum, perspiration and/or other cosmetics present on the skin into the cosmetic stick when the oil content is small (with cosmetics in the powdery or medium ranges).

SUMMARY OF THE INVENTION

The present invention overcomes the above problems of the prior art and aims to provide a novel coated pigment which is easily dispersed in water and exhibits water-repellent property after the water is evaporated and a cosmetic material comprising said novel pigment.

Another object of the present invention is to provide a novel cosmetic material which gives refreshment and/or smoothness depending on the purpose and use, acts to last the make-up, is resistant to water, and can be used in a broader range of compound ratio.

In other words, the present invention provides a novel cosmetic material suitable for use in stick-type cosmetics, particularly of pencil form, which gives improved finish, touch and feeling in make-up not found in the conventional products as the powder of coated pigment can be blended at a high concentration ratio.

For achieving the objects, the coated pigment according to the present invention is characterized in that it is coated with metallic soap on the surface and contains water. As a preferred example, the pigment characteristically contains more than 20% by weight of water in the total weight, and includes one or more than two pigments selected from the group of mica type pearl pigments and pearl pigments of bismuth oxychlorides type. Metallic soap to be coated on the pigment surface may be selected from compounds expressed by a general formula of (RCOO)nM wherein R represents a straight chain, branched, saturated or, unsaturated hydrocarbon radical having more than 6 carbon atoms; M, aluminum or zinc; n the valency of the metal.

The cosmetic material according to the present invention is characterized in that it is comprising of pigments which is coated with metallic soap on the surface and contains water. A preferred example of the cosmetic material contains said coated pigments in an amount ranging from 20 to 95% by weight of total weight. Said coated pigment is characterized by the water content of more than 20% by weight of the total weight of the pigment.

DETAILED DESCRIPTION OF THE INVENTION

The coated pigment of the present invention will now be described in further detail. The coated pigment according to the present invention comprises pigment, metallic soap and water, said pigment coated with metallic soap on the surface and containing preferably 20 wt.% or more of water.

The pigment according to the present invention may include pearl pigments of mica group such as titanium dioxide-coated mica and colored titanium dioxide-coated mica; and pearl pigments of bismuth oxychlorides such as colored bismuth oxychloride. One or more than two pigments are selected and blended according to the preparation process described below. As examples of titanium dioxide-coated mica, colored titanium dioxide-coated mica and colored bismuth oxychloride etc. available on the market, there are Flamenco series (by the Mearl Corporation), TIMIRON COLORS (by MERCK) as titanium dioxide-coated mica, Timica Luster Pigments (by MEARL). Cloisoneé series (by MEARL), COLORON series (by MERCK), SPECTRA-PEARL PIGMENTS (by Mallinckrodt) as colored titanium dioxide-coated mica and MIBIRON COLORS series (by MERCK) as colored bismuth oxychloride. Titanium dioxide-coated mica generally refers to pigment with pearl-like gloss which comprises mica coated with a titanium layer and which becomes iridescent (exhibits interference color) depending on the thickness of the titanium layer. Colored titanium dioxide-coated mica refers to pearl-like pigment which is obtained by reacting for adsorption pigment on the titanium layer of said titanium dioxide-coated mica and which has improved chromophoric strength and better glossiness.

The metallic soap which constitutes the coated pigment according to the present invention may be selected from compounds which are expressed by the general formula of (RCOO)nM wherein R represents a straight chain, branched, saturated, or unsaturated hydrocarbon group having more than 6 carbon atoms; M, aluminum or zinc; and n the valency of the metal.

The compound is to be coated on the pigment surface during the preparation of the coated pigment according to the present invention described below. When blended in cosmetic materials, a compound of said general formula wherein R is an aliphatic group having 8 to 20 carbons is a preferable metallic soap in view of stability, water-repellent property, moisturizing power, degree of absorption to the pigment and ease in handling as the raw material. Particularly, metallic soaps comprising stearic acid, isostearic acid, myristic acid palmitic acid and lauric acid, oleic acid as the aliphatic group and a metal such as aluminum, and zinc as the salt part are preferred, and one or more than two of these are selected and blended.

The ratio of the pigment to the metallic soap in the composition of the coated pigment according to the present invention is preferably in the range of 1 to 0.01 to 0.1 in weight. If the treated pigment contains the metallic soap in an amount exceeding said ratio, it is likely to cause flocculation of pigment particles, or the metallic soap tends to float or become freed being not adsorbed on the pigment surface. If the amount of metallic soap is less than the ratio given above, the coating will yield no effect. For example, even when the pigment is blended in a cosmetic material, the product will not have sufficient water-repellent property or lipophilic property.

The important point of the present invention is that the pigment coated with metallic soap contains water by 20 wt.% or more. Because of the water content, the pigment can be easily dispersed in water. Inclusion of the water in the pigment will obtain an excellent and a novel pigment which will be easily dispersed in the water and exhibit water-repellency after the water content has been evaporated. When the water content is less than 20 wt.%, the pigment may, upon dispersion in water, immediately float in the supernatant or may be unevenly dispersed. Although it is more or less possible to improve the uneven dispersion by using a surfactant, the pigment will not exhibit sufficient water-repellency after the water content is evaporated. If the water content is extremely high, the pigment concentration becomes so thin that it becomes necessary to remove the water again in order to raise the concentration to suit the intended use. With the novel pigment of the present invention, the water content thereof should preferably be in the range of 50±10% by weight in view of its production requirements and the products quality.

The process for preparing the coated pigment according to the present invention will now be described below.

Using aliphatic acid alkaline salt and metal salt in the theoretical equivalent ratio of 1:4:to 1:10, the components are reacted in an aqueous phase to cause the metallic soap to coat the pigment surface. More concretely, aliphatic acid alkaline salt is dissolved in the purified water at a temperature higher than 80° C., preferably at about 80° C. to 90° C. Pigment is then dispersed uniformly in the mixture, gradually added with metal salt dissolved in pure water at a temperature between 5° to 90° C. while stirring, and reacted to obtain coated pigment containing water by filtering if necessary. As another method, metallic salt is dissolved in the purified water at a temperature higher than 80° C., or more preferably at 80° C. to 90° C., and then added with pigment for uniform dispersion therein, further added gradually while stirring with a mixture of purified water and aliphatic acid alkaline salt dissolved at 80°-90° C., reacted, and filtered depending on the need to obtain a coated pigment containing water. Aliphatic acid alkaline salt and metal salt in the preparation process mentioned above are used in the theoretical equivalent ratio of 1:4 or more, preferably in the range of between 1:4 to 1:10. If the amount of metal salt is less than said range, the coated pigment is likely to be suspended in the surface boundary of the aqueous phase with the air instead of being dispersed even if the metallic soap forms a coating on the pigment surface by adsorption. This is because the metallic soap is inherently water-repellent. On the other hand, if the amount of metal salt used exceeds said range, there will be an excessive amount of reaction residue to present hazardous problems in saftey. It also requires repeated washings to remove the residue and is thus uneconomical.

Aliphatic acid alkaline salt to be used in the process for preparing the coated pigment according to the present invention may be one or more than two kinds of or compounds of aliphatic acid selected from straight-chain, branched, saturated, unsaturated higher aliphatic acids having 9 to 21 carbon atoms, for example, stearic acid, isostearic acid, myristic acid, palmitic acid, lauric acid, oleic acid. Alkaline salt may be sodium salt, potassium salt, etc.

Metal salt used in the process may be selected from aluminum and zinc salts. Examples of such metal salts are aluminum chloride, aluminum sulfate, potassium aluminum sulfate, zinc chloride, zinc sulfate, etc.

The amount of water to be used in the process is preferably about 9 times in weight of the pigment. Water in excess of said amount makes the process uneconomical, whereas if the amount of water is small, it will make the agitation difficult, causing the pigment particles to easily flocculate and making it difficult to obtain pigment uniformly coated with metallic soap.

The following examples concern preparation of coated pigments according to the present invention.

PREPARATION EXAMPLE 1

(i) 5.1 kg of aluminum sulfate was added to 350 kg of purified water, mixed and heated to 80° to 90° C. to dissolve aluminum sulfate. The resultant mixture was added with 18.2 kg of yellow, iron oxide and 31.8 kg of red iron oxide and dispersed uniformly and well to obtain A.

(ii) In a separate vessel, 2.8 kg of sodium stearate was added to 100 kg of purified water, heated and dissolved while being maintained at 80°-90° C. to obtain B.

(iii) Then, B was gradually added to A while stirring. Upon completion of addition, decantation was repeated 4 times to remove the residual salt from the reaction product. Without filtration, 500 kg of pigment coated with 5% of aluminum stearate and containing 90% of water was obtained.

PREPARATION EXAMPLE 2

(i) 12.2 kg of zinc sulfate was added to 350 kg of purified water, mixed and heated to 80°-90° C. to dissolve the same. 2.5 kg of red iron oxide, 8.3 kg of ultramarine, 10.8 kg of titanium oxide, 3.3 g of iron black, 15 kg of talc, and 10 kg of sericite were added to the resultant mixture and dispersed uniformly and well to obtain A.

(ii) In a separate vessel, 2.6 kg of sodium stearate was added to 100 kg of purified water, mixed and heated to 80°-90° C. to dissolve the same to obtain B.

(iii) B was added to A slowly while stirring. Upon completion of addition, decantation was repeated 10 times to wash and remove the residual salt. The resultant mixture was filtered to obtain 100 kg of pigment coated with 5% zinc stearate and containing 50% by weight of water. The theoretical equivalent ratio of aliphatic acid alkaline salt to the metal salt was 1:10.

PREPARATION EXAMPLE 3

(i) 6.1 kg of zinc sulfate was added to 350 kg of purified water mixed and heated to 80°-90° C., dissolved, and then added with 35.5 kg of ultramarine, 3.6 kg of yellow iron oxide, 2.3 kg of red iron oxide, 4.1 kg of iron black and 4.5 kg of titanium dioxide-coated mica (Flamenco Superpearl available from MEARL), dispersed uniformly and well to obtain phase A.

(ii) In a separate vessel, to 100 kg of purified water was added 2.6 kg of sodium myristate, and the resultant mixture was heated to 80°-90° C., and dissolved to obtain Phase B.

(iii) Phase B was gradually added to Phase A under stirring, washed 4 times by decantation after completion of addition, removed of residual salt, and filtered to obtain 100 kg of pigments coated with 5% of zinc myristate and containing 20% of water.

PREPARATION EXAMPLE 4

(i) 2.8 of sodium stearate was added to 350 kg of purified water mixed and heated to 80°-90° C., dissolved, added with 33 kg of iron black-colored titanium dioxide-coated mica (Timica Nu-Antique Silver available from MEARL), 7 kg of titanium dioxide-coated mica (Flamenco superpearl 100 available from MEARL), and 10 kg of iron black, and dispersed uniformly and well to obtain Phase A.

(ii) In a separate vessel, 4.08 kg of aluminum sulfate was added to 100 kg of purified water, mixed and dissolved at 60°-70° C. to obtain Phase B.

(iii) Phase B was gradually added to Phase A while stirring, washed 4 times by decantation upon completion of addition, removed of residual salt, and filtered to obtain 100 kg of pigment coated with 5% aluminum stearate and containing 50% of water. The theoretical equivalent of aliphatic acid alkaline salt to metal salt was 1:4.

PREPARATION EXAMPLE 5

(i) 7.7 kg of aluminum sulfate was added to 350 kg of purified water, mixed, heated to 80°-90° C., dissolved, added with 0.15 kg of ultramarine, 0.3 kg of yellow iron oxide, 1.0 kg of red iron oxide, 7.4 kg of titanium oxide, 8.8 kg of talc, 8.85 kg of titanium dioxide-coated mica (Timiron Super Silk MP-1005 available from MERCK), and 23.5 kg of sericite, and dispersed uniformly and well to obtain Phase A.

(ii) In a separate vessel, 2.8 kg of fatty acid sodium was added to 100 kg of purified water, wherein sodium stearate and sodium oleate are mixed at 1:1, and the resultant mixture was heated and dissolved at 80°-90° C. to obtain Phase B.

(iii) Phase B was gradually added to Phase A under stirring, washed 4 times by decantation upon completion of addition, removed of residual salt, and then filtered to obtain 77 kg of pigments coated with 7.5% mixture of aluminum stearate and aluminum oleate and containing 35% of water.

PREPARATION EXAMPLE 6

(i) 2.6 kg of sodium stearate was added to 350 kg of purified water, mixed, dissolved at 80°–90° C., added with 1.08 kg of yellow iron oxide, 0.25 kg of red iron oxide, 0.37 kg of iron black, 18.5 kg of calmin-colored titanium dioxide-coated mica (Chloisonné Red available from MEARL), 9 kg of oxide iron-colored bismuth oxychloride (Mimilon) Color Red available from MERCK), and 20.8 kg of mica, and dispersed uniformly and well to obtain phase A.

(ii) In a separate vessel, 6.1 kg of zinc sulfate was added to 100 kg of purified water, and dissolved while being heated to 60°–70° C. to obtain Phase B.

(iii) Phase B was gradually added to Phase A while stirring, washed 4 times by decantation upon completion of addition, removed of residual salt, and then filtered to obtain 100 kg of pigment coated with 5% zinc stearate and containing 50% of water.

PREPARATION EXAMPLE 7

(i) 2.8 g of sodium stearate was added to 350 g of purified water, mixed, dissolved at 80°–90° C., added with 33 g of iron black-colored titanium dioxide-coated mica (Timica Nu-Antique Silver available from MEARL), 7 g of titanium dioxide-coated mica (Flamenco Superpearl 100 available from MEARL), and dispersed uniformly and well to obtain Phase A.

(ii) In a separate vessel, 5.1 g of aluminum sulfate was added to 100 g of purified water, mixed, and dissolved at 60°–70° C. to obtain Phase B.

(iii) Phase B was gradually added to Phase A while stirring, washed 4 times by decantation upon completion of addition, removed of residual salt, filtered and then dried to obtain about 53 g of pigment coated with 5% of aluminum stearate and containing 5% of water.

PREPARATION EXAMPLE 8

(i) 0.28 g of sodium stearate was added to 350 g of purified water, mixed and heated to 80° to 90° C. to dissolve sodium stearate. The resultant mixture was added with 33 g of iron black-colored titanium dioxide-coated mica (Timica Nu-Antique Silver available from MEARL), 7 g of titanium dioxide-coated mica (Flamenco Superpearl—100 available from MEARL) and 10 g of iron black, and dispersed uniformly and well to obtain Phase A.

(ii) In a separate vessel, 0.51 g of aluminum sulfate was added to 100 g of purified water, mixed, and dissolved at 60°–70° C. to obtain Phase B.

(iii) B was gradually added to A while stirring, washed 4 times by decantation upon completion of addiiton, removed of residual salt, and then filtered to obtain about 62 g of pigment coated with 0.5% of aluminum stearate and containing 20% of water.

PREPARATION EXAMPLE 9

(i) 5.1 kg of aluminum sulfate was added to 350 kg of purified water, mixed and heated to 80°–90° C. to dissolve aluminum sulfate. The resultant mixture was added with 0.9 kg of yellow iron oxide, 1.6 kg of red iron oxide, 16.7 kg of titanium oxide, 30.8 kg of talc, and dispersed uniformly and well to obtain A.

(ii) In a separate vessel, 2.8 kg of sodium stearate was added to 100 kg of purified water and dissolved at 80°–90° C. to obtain B.

(iii) B was gradually added to A while stirring, washed 4 times by decantation upon completion of addition, removed of residual salt and filtered to obtain 100 kg of pigment coated with 5% of aluminum stearate and containing 50% of water.

The coated pigment thus obtained in accordance with the present invention is a novel and excellent pigment which has a solid coating of metallic soap physically and chemically formed on its surface by absorption and which contains water. Thus it can be easily dispersed in water and once the water content is evaporated after dispersion, the pigment will exhibit water-repellent property.

The coated pigment with its excellent properties according to the present invention is applicable to various uses such as paints, printing ink, cosmetics, and coloring materials.

The effects of the coated pigment of the present invention will be explained in more detail. Its main characteristics lies in that the metallic soap is physically and chemically absorbed on the surface of the pigment, whereby even if the pigment is dispersed in the product system the coating will remain integral with the pigment. On the conventional pigment coated with metallic soap and containing no water is already formed an air layer on its surface so that when the pigment is dispersed in water, substitution of the air with the water can not be easily achieved, making dispersion of the pigment difficult. Whereas because the present coated pigment is prepared in an aqueous phase the pigment surface remains moisturized with water (in other words, the boundary surface of the coated pigment is covered completely with water), its dispersion in water becomes all the more easy. Moreover, the theoretical equivalent ratio of aliphatic acid alkaline salt and metal salt generally employed in the conventional art is such that when the coated pigment is dispersed in an aqueous phase, it becomes suspended in the upper layer of the aqueous phase and easily contacts with air. This makes dispersion of the pigment difficult in water. However, the present invention coated pigment contains aliphatic acid alkaline salt and metal salt in a suitable ratio and is therefore more reaidly dispersed in water. It is assumed that the residual salt which did not participate in the reaction is responsible for the foregoing as it is somehow adsorbed on the pigment surface.

In order to demonstrate the superior features of the coated pigment according to the present invention, results of experiments on (A) its dispersion in water, and (B) the water-repellent property after application are shown in Table 1.

(Methods)

(A) Regarding dispersion in water:
10 g each of samples were dispersed in a beaker (200 ml) containing 20 ml of water, agitated for 3 minutes using Disper (3,000 rpm) and left standing. The dispersion property was observed.

(B) Water-repellent property after application:
About 1 g each of samples was evenly applied on the upper-arm of a subject (3 cm×3 cm). When the coated surface dried completely, the surface was washed with running water from the tap for 5 minutes. Wettability of the pigment was observed with naked eyes.

(Samples)

(a) Conventional commercial colored titanium dioxide-coated mica (Cholsonn Red available from MEARL) with 5% coating of aluminum stearate by the conventional solvent method. The coated pigment contained no water.

(b) Conventional commercial pigment (a) with 5% coating of aluminum stearate containing 0.5% surfactant (polyoxyethylene nonylphenol, P.O.E. 15 mol). The coated pigment contained no water.

(c) Coated pigment prepared according to the same process as described in Preparation Example 7 which is provided with 5% coating of aluminum stearate and which contains 5% water. (The theoretical equivalent of aliphatic acid alkaline salt to metal salt is given as 1:5).

(d) Coated pigment prepared according to the same process as described in Preparation Example 3 which is provided with 5% coating of aluminium stearate and which contains 20% of water. (The theoretical equivalent of aliphatic acid alkaline salt to metal salt is given as 1:5). (Equivalent product of the present invention).

(e) Coated pigment prepared according to the same process as described in Preparation Example 9 which is provided with 5% coating of aluminum stearate and which contains 50% of water. (The thoretical equivalent of aliphatic acid alkaline salt to metal salt is given as 1:5). (Equivalent product of the present invention)

(f) Coated pigment prepared according to the same process as described in Preparation Example 1 which is provided with 5% coating of aluminum stearate and which contains 90% of water. (The theoretical equivalent of aliphatic acid alkaline salt to metal salt is given as 1:5). (Equivalent product of the present invention)

(g) Coated pigment prepared according to the same process as described in Preparation Example 8 which is provided with 0.5% coating of aluminum stearate and which contains 20% of water. (The theoretical equivalent of aliphatic acid alkaline salt to metal salt is given as 1:5).

(h) Coated pigment prepared according to the same process as described in Preparation Example 5 which is provided with 7.5% coating of aluminum stearate and which contains 35% of water. (Equivalent product of the present invention)

(i) Coated pigment prepared according to the same process as described in Preparation Example 1 which is provided with 5% coating of aluminum stearate and which contains 50% of water. (The theoretical equivalent of aliphatic acid alkaline salt to metal salt is given as 1:1. Aluminum sulfate in Example 1 weighs 1.02 kg).

TABLE 1

| Samples | A<br>Dispersion in water | B<br>Water-repellency after application |
|---|---|---|
| (a) Conventional pigment processed with Al stearate and containing no water | X<br>(do not disperse, become suspended) | ⊚<br>(excellent) |
| (b) Conventional pigment processed with Al stearate activator and containing no water | △<br>(disperse a little, viscosity increases in part) | X<br>(no water repellency) |
| (c) Pigments coated with 5% Al stearate and containing 5% water | X<br>(do not disperse, become suspended) | ⊙<br>(water-repellency) |
| (d) Pigments coated with 5% Al stearate and containing 20% water (equivalent to present invention substance) | ⊙<br>(disperse uniformly, excellent) | ⊙<br>(excellent) |
| (e) Pigments coated with 5% Al stearate and containing 50% water (equivalent to present invention substance) | (disperse uniformly, excellent) | (excellent) |
| (f) Pigments coated with 5% Al stearate and containing 90% water (equivalent to present invention substance) | ⊙<br>(disperse uniformly, excellent) | ⊙<br>(excellent) |
| (g) Pigments coated with 0.5% Al stearate with containing 20% water | ○<br>(disperse) | X<br>(no water repellency) |
| (h) Pigments coated with 7.5% Al stearate and containing 35% water (equivalent to present invention substance) | ⊙<br>(disperse uniformly, excellent) | ⊙<br>(excellent) |
| (i) Pigments coated with 5% Al stearate and containing 50% water | X<br>(do not disperse, become suspended) | ⊙<br>(excellent) |

As is evident from Table 1, samples (a) and (b) of the conventional coated pigments and samples (c) and (g) which are not sufficient in metallic soap coating and water content show an inferior result at least either in dispersion property in water or water-repellency after application. In case of the comparative sample (i) wherein the theoretical equivalent of aliphatic acid alkaline salt to metal salt is given as 1:1, the pigment exhibits water-repellency, does not disperse in water but is suspended in the phase On the other hand, samples (d) through (f) and (h) of the equivalent products according to the present invention which have sufficient metallic soap coating and water content show uniform dispersion water and excellent water-repellency after application. It is therefore demonstrated that the coated pigment according to the present invention fulfills the two requirements at the same time.

It was confirmed by another experiment that a coated pigment with 20% water content cannot be provided with 11% coating of metalic soap.

In the theoretical equivalent ratio the metal salt is more eleven times as much as aliphatic acid alkaline salt, there will be excess reaction residues, as mentioned above, so much so that it would require repeated washings, and thus become uneconomical.

The description of cosmetics and the process of preparing the same will now be given.

Cosmetics according to the present invention are obtained by blending the coated pigments mentioned in the foregoing. Such cosmetics, when they are an aqueous phase will give refreshment and freshness to the skin and are resistant against perspiration, tears, water, sebum, etc. after application. Because of their water-repellency, they do not come off easily but last longer when applied as a make-up and are water-resistant. Moreover, the cosmetics according to the present invention, when they are an oily phase are free of stickiness and "gathering" causes by sebum, defects typically found in the conventional products, and instead provide a moisturizing feeling which is the typical advantage of an oily cosmetic. Thus, the cosmetics according to the present invention combine the advantage of both aqueous and nonaqueous products available on the market and overcome the disadvantages of each system.

Amount of the coated pigment to be blended in the cosmetics according to the present invention may be suitably selected depending on the purpose, use and form. With an aqueous product a preferable amount of the pigment is in the range of between 20 and 95 weight % of the total weight (calculated on the basis that the pigment contains 50% of water.)

In order to demonstrate the superior properties of the cosmetics accoridng to the present invention as compared to the conventional products, practical tests were conducted with a panel of 20 experts beauticians. The results are shown in Table 2. As a sample of the present invention, an emulsion type foundation of Example 1 to be described later was selected and as a sample of the conventional products, a commercial emulsion type foundation and an oily foundation were used. Table 2 shows the results of evaluation by said 20 experts who used said 3 samples for 3 weeks, expressed in a profile of practical test plotted by the mean value of points given by the panel members.

Points of evaluation included refreshment stickness, moisturing effect, water-resistance, and whether the make-up lasts longer after application.

Components of the stick type cosmetic according to the present invention using above mentioned coated pigment will be described in detail. The metallic soap coated pigment as the essential component which contains water is used as the raw material. However, when blended in the stick type cosmetic during the manufacturing process to be described later, the pigment coated with metallic soap will hardly contain water in the final stage. The amount of the pigment to be blended ranges from 6 to 64 weight % of the toal weight. Amount of Gypsum, another essential component, ranges from 14 to 60 weight %, preferably from 18 to 52 weight %. If desired, a pigment (as an extender pigment or coloring pigment) may be blended in an amount of from 0.5 to 32 weight % as powder component. Major additives include 1 to 50 weight % of an oil content and 0.5 to 10 weight % of a moisture retaining agent, with other additives such as suitable amount each of perfume, antioxidant, disinfecting agent, and antiseptic.

Preferable gypsum to be used in the present invention includes anhydrous gypsum expressed by $CaSO_4$ and/or hemyhydrous gypsum expressed by $CaSO_4 \cdot \frac{1}{2}H_2O$, irrespective of the crystalline form of $\alpha$, $\beta$, $\beta\gamma$, $\gamma$, etc.

TABLE 2

| Points of evaluation | | | 0 | 1 | 2 | 3 | 4 | 5 | 6 | 7 | 8 | 9 | 10 | |
|---|---|---|---|---|---|---|---|---|---|---|---|---|---|---|
| when applying | refreshment | no | | | Δ | | | | | | XO | | | yes |
| | stickiness | yes | | | | Δ | | | | | XO | | | no |
| after application | stickiness | no | | | | | | X | | | OΔ | | | yes |
| | water-repellency | no | | | | | X | | | | ΔO | | | yes |
| | lasting | | | | | | Δ | X | | | | O | | yes |

In the Table 2, symbols x, Δ and O represent the following cosmetics:

x: conventional emulsion type foundation
Δ: conventional oil type foundation
O : emulsion type foundation of the present invention As indicated in Table 2, as far as cool and refreshment and stickness at the time of application are concerned, the sample of the present invention shows similar results as those of the conventional emulsion type foundation. The present invention product shows better result in the moisturizing effect after application and is much better in water-resistance and lasts longer than the conventional emulsion type product. When compared with the conventional oily foundation, the product according to the present invention is superior in the cool and freshness feeling and water-resistance and lasts longer as a make-up. Whereas 10 out of 20 panel members complained of the "gathering" of the conventional oily foundation caused by sebum, no such gathering was experienced with the present invention.

As is evident from these evaluation results, the present invention provides cosmetics of an extremely high quality.

In case the cosmetic comes in the form of a stick, it should contain gypsum as an essential component. Because of the coated pigment according to the present invention, said stick type cosmetic is improved over the defect of the conventional product that the gypsum containing product tended to shrink. Further, the product is superior in moldability and water-repellency.

Thus, shrinkage of the product can be prevented without using spherical particles which are dispersible in water and the stick type cosmetic with excellent water-repellency can be obtained.

Any known materials used in the cosmetic industry may be suitably selected and used as the pigment for the powder component or additives such as an oil moisturizer and retaining agent. Each component of said stick type cosmetic may be suitably selected and combined depending on the use of the final product. For moldability and improved feeling and touch in use, composition of hemihydrous gypsum and at least either one of mica coated with titanium oxide or mica of coloring pigment coated with chromophric titanium oxide as the pearl pigment of mica group in said range of ratio gives excellent results.

The important feature of the present invention lies in the following; in the conventional stick type product (especially an integrally molded product in the form of a pencil) wherein pigments such as talc or kaolin or other untreated pearl pigment which are generally used in cosmetics are blended as the powder component with gypsum, excessive shrinkage or bending occurs at the time of molding or inferior fluidity at the time of filling is observed. Use of two essential components of the coated pigment powder and gypsum in the present invention overcomes these disadvantages.

Manufacturing process for the stick type cosmetic according to the present invention will now be described in detail. Powder component comprising surface treated pigment powder of the present invention (containing water), and gypsum is dispersed in water or a mixture of water and additives to obtain a fluidized slurry. Amount of water or a mixture of water and additives is used in 1.3 to 1.8 (preferably 1.5 to 1.7) weight ratio as against one unit of the powder component. If necessary, the mixture may be heated and dissolved. The fluidized slurry must be adjusted so that its viscosity measured by a rotary viscometer within 4 minutes after preparation of the slurry is 4,000 cp. or less. Slurry will be charged in a mold having a cavity in the form of a column. For an ordinary stick-type cosmetic, the cross section of the cavity in the mold is in the range of 12 to 490 mm$^2$ and the height 5.2 mm or more, preferably between 5.2 and 50 mm, which is expressed as A×1.5 wherein A is the cross section. In case a pencil shaped cosmetic is desired, the cross section of the cavity should range from 3 to 80 mm$^2$ (with a tubular form, the diameter is 2 to 10 mm, more preferably 5 to 8 mm) and the height from 30 to 120 mm. The cavity may have a bottom or may be a through-hole without a bottom. The slurry may be charged into the mold in various ways. For example, it may be poured, or filled by means of a nozzle or under pressure. In case of filling under pressure, a filling apparatus disclosed in the Japanese Patent Application No. 201271, 1982 (filed by the present applicant) will be used. More particularly, the apparatus comprises a container for said content (fluidized slurry) and a piston having an outer diameter which is very close to the inner diameter of said container. The piston may be of any arbitrary shape or material, and is pressed into the container. Because one or more of said column-like through-holes are provided in the direction of piston's advance, the content in the container flows backward to be filled in said column cavity immediately upon pressing by the piston. A pipe-like member for retaining the shape of the content may be provided in the apparatus instead of the piston. As compared with the pouring or filling by means of a nozzle, this method of filling under pressure is more advantageous in that the slurry may be charged into pipe-like mold having a very small and narrow opening such as in the case of a pencil-type cosmetic, or that slurry having a higher viscosity may also be easily charged. Moreover, it is capable of charging into plural cavities at the same time in a short period of time.

In hardening thus charged slurry, the mold is left standing at a temperature at 5°–30° C. for more than 30 minutes, preferably from 50 minutes to 4 hours. For drying, both the molded product and the mold are to be dried concurrently. In case the molding has a bottom, the open end should always be placed at the top so that water, etc. may be evaporated only from the open end. In case the mold is of a through-hole type, one open end should be closed until the other end placed at the top so that water, etc. may be evaporated from one of the ends alone. Drying temperature ranges from 40° to 60° C., the humidity less than RH 80%, preferably from RH 50% to 75%. Drying time should be preferably adjusted depending on the cross section and height of the molded product. Depending on the strength of the molded product, vacuum drying may be employed to radically reduce the drying time. Because of dehydrating process mentioned above, the pigment coated with metallic soap in the final product will be substantially free of water content.

When a pencil-type cosmetic is desired, one or plural member of shape-retainers for the molded product in the form of a bottom-less pipe may be provided as a piston in said mold. When such members are pressed in the slurry container, the slurry will flow backward to the members to be filled therein. This way, the slurry may be integrally molded. Such a retainer member for the molded product may be made of resin (thermosetting resins such as polyethylene, polypropylene, nylon), composite materials which can be ground, wood, metal (aluminum, etc.), alloy (alloys of iron, copper, aluminium, etc.), paper, rubber, glass, ceramics, porcelain, etc. Its thickness should range from 1.5 to 2.5 mm. Examples of composite materials which can be ground may include olefin polymers such as those disclosed in the Japanese Patent Application Laid-open No. Sho 55-81810, wax, mixtures of inorganic powders. (These composite materials, if formed tubular, may provide, as mentioned earlier, a stick-type cosmetic molded integrally with the mold without removing the mold after filling, hardening and drying processes.) Said retainer member may be in any desired form other than a pencil to suit the appearance of the stick-type cosmetic to be produced. Ths retainer member may be ground in advance or it may be processed after the content is filled.

In the manufacturing process of the present invention described above, a hardening-retardant or hardening-accelerator may be added to water or said mixture. The hardening retardant is used to delay hardening of gypsum and may include phosphoric salt, alkaline salt of organic dibasic acid, glue, gelatin, mono- and polyhydric alcohols. Hardening accelerator is used to promote hardening of gypsum and may include sodium chloride, potassium chloride, potassium sulfate, potassium alum, etc.

Further, if necessary, the molded product dried and released from the mold may be immersed in a mixture comprising volatile solvent and oily substance and/or wax (immersion time and the concentrations of the oily substance and wax in the volatile solvent should be adequately adjusted) and then the solvent may be removed by drying, whereby the content of oily substance in the product cosmetic may be increased or the product may be coated with wax on the surface.

As has been described in the foregoing, the manufacturing process of stick-type cosmetics according to the present invention is characterized in that said coated pigment and gypsum as the essential components of mixed powder are dispersed in water or a mixture of water and additives to obtain fluidized slurry, which is filled in the cavity in the form of a column provided in the mold, hardened and dried.

The effects of the present invention will now be described. With the stick-type cosmetic according to the present invention, defects of the conventional oil gel type cosmetics such as too much oiliness or that of coming off too easily can be overcome since the cosmetic according to the present invention may contain the powder component in a wider range from the medium to powder ranges. Moreover, its touch and effect in make-up may be variable over a wider range including those similar to the conventional stick-type cosmetics to those similar to the cake-type cosmetics. Table 3 shows results of tests where a panel of 20 beauty experts used the samples A, B and C for 3 weeks for comparison. (The results are expressed in a profile of organoleptic test scores plotted by the mean of evaluation by the panel members.)

In the Table, symbols ○, X, and Δ represent the following stick-type cosmetics:

○ : conventional eye-shadow stick of oil gel type

X: conventional eye-shadow stick disclosed in Example 1 of the Japanese Patent Application No. Sho 57-201271

Δ: stick eye-shadow of the present invention described in Example 4.

TABLE 3

| Points of evaluation | | 0 | 1 | 2 | 3 | 4 | 5 | 6 | 7 | 8 | 9 | 10 | |
|---|---|---|---|---|---|---|---|---|---|---|---|---|---|
| 1. hardness of core when applying | hard | | | | | | ○ | X | Δ | | | | soft |
| 2. heaviness of tip when applying | heavy | | | | ○ | X | | | Δ | | | | light |
| 3. ease in spreading | hard to spread | | | | | | ○ | X | | Δ | | | easy to spread |
| 4. feel in spreading | oiliness | | | ○ | | | | X | Δ | | | | powderiness |
| 5. finish (matting) | oiliness | | | ○ | | Δ | X | | | | | | powderiness |
| 6. lasting | no | | | | ○ | | | X | | Δ | | | yes |
| 7. water-resistance | no | | X | | | | | | | Δ | ○ | | yes |
| 8. taking on color | bad | | | | | X | | | ○ | Δ | | | good |

As is evident from Table 3, the stick eye-shadow of the present invention is clearly superior in use (items 1 through 3), touch, finish, lasting as a make-up, taking on color as compared with the conventional products A and B. It is also apparent that its water-resistance is greater than that of the sample B by a great margin.

Figure 1:
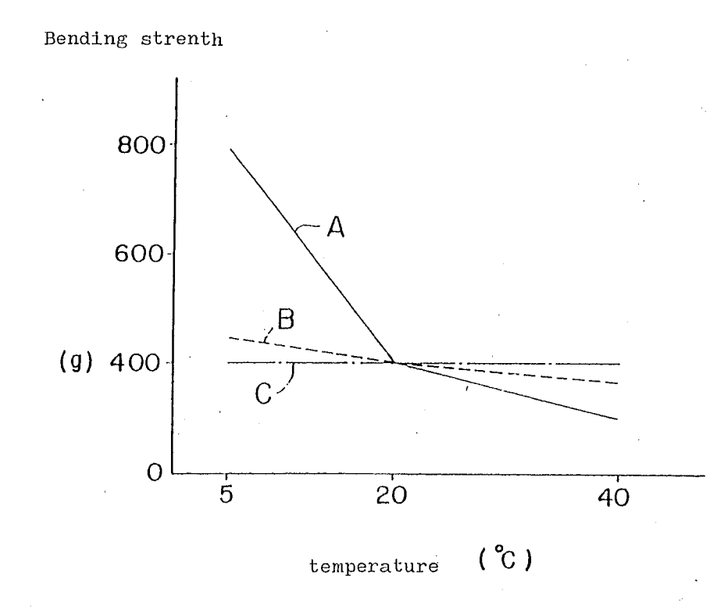
The accompanying drawing is a graph showing the bending strength of stick-type cosmetics at different temperatures.

One of the major characteristics of the present invention stick-type cosmetic is its high thermal stability. Conventional stick-type cosmetics are highly dependent on temperature; for example, they become very sticky and easily broken when used at high temperatures (around 40° C.). On the other hand, when used at low temperature (around 5° C.), they become hard and difficult to paint. As a result, they caused inconveniences in use such as they were too sticky and easily broken during summer and difficult to paint in winter. The main cause for such inconveniences arise from the fact that the main component is made of wax, a substance susceptible to temperature changes. Moreover, there is this paradoxical fact that the higher the temperature dependency is, the better the cosmetic feels. The stick-type cosmetic according to the present invention is molded into a stick utilizing the nature of the powder component (more concretely, the crystalline structure of gypsum). Thus it is hardly affected by temperature as shown in the drawing. The drawing is a graph showing the measurement results of the bending strength of the present invention stick-type cosmetic at different temperatures. In the drawing, letter A represents the conventional eye-shadow stick of oil gel type, B the conventional eye-shadow stick disclosed in Example 1 of the Japanese Patent Application No. Sho 57-201271, and C the eye-shadow stick according to Example 4 of the present invention. The bending strength was measured by the load (in g) at which eye-shadow stick with an outer diameter of 6 φmm and of length 35 mm were broken at the center of the 20 mm span. It is understood from the graph that the conventional products show extremely high temperature dependency whereas the stick-type cosmetic according to the present invention is less susceptible to temperature changes.

As mentioned above, gypsum is used as the structural component of the stick-type cosmetic according to the present invention. It is noted that the conventional stick-type cosmetic which contains inorganic or organic powder (including soluble organic polymeric substances which may be solidified after solvent is evaporated, such as PVA, PE, CMC) alone as the structural component (e.g. Japanese Patent Applications Laid-open No. Sho 52-12934, No. Sho 54-80428, No. Sho 54-163831, etc.) is extremely vulnerable against impact caused by dropping. On the other hand, the pencil-type cosmetic as described in Example 4 is greatly improved on the impact strength.

Conventional stick-type cosmetics ranging of from medium to powder forms become caked on the surface by sebum, perspiration, etc. on the skin when they are directly applied. In the case of the present invention, the powder component which holds the stick structure can be sufficiently prevented from becoming closely packed by forming the stick in a pencil form. At the same time, its bending strength can be maintained and caking phenomenon can be prevented.

The Japanese Patent Publication No. Sho 45-36595 discloses a cosmetic comprising burnt gypsum. Said Patent relates to a process for manufacturing a cake type make-up which comprises the steps of kneading burnt gypsum which is a known cosmetic material, and pouring the mixture in a pan to be solidified. The content is filled in a plate-like container having a large opening which is peculiar to such a cake type cosmetics. It is characteristically applied using a puff or brush. On the other hand, the present invention provides stick-type cosmetics in a pencil form which can be applied without using any tools. The present invention further relates to a manufacturing process for stick-type cosmetics which can be molded integrally with a pipe-like mold, by filling the content into the mold through its extremely small opening. Thus, the present invention is essentially different from the patent mentioned above.

Examples of the present invention will now be described. Ratio of the components is expressed in parts by weight. (Figures in parentheses given after the weight part represent the ratio by weight percent of the products after water is removed.)

EXAMPLE 1

Emulsion-type Foundation

Using the materials listed in Table 4, a foundation product was prepared according to the following process.

(1) A was charged into the dissolving tank and the soluble components were dissolved by heating the solution to 75° to 85° C. The mixture was then agitated at high speed to form liquid phase (2) B was separately charged into the reaction tank, mixed, heated to 75°–85° C., dissolved and formed oil phase.

(3) The liquid phase in the dissolving tank was added slowly to the oil phase in the reaction layer while agitating, and emulsified. Upon completion of the liquid phase addition, the reaction tank was cooled to 40°–50° C., added with C, further cooled to 35° C., whereupon cooling and agitation were suspended. The product was removed from the reaction tank.

EXAMPLE 2

Eye-Color (liquid type)

Using the materials listed in Table 4, a liquid type eye-color product was prepared according to the following process.
(1) A was charged into the emulsifying tank, uniformly mixed while maintaining the temperature between 50° and 60° C.
(2) B was charged separately into the dissolving tank and heated to 50°–60° C.
(3) The mixture (2) was added to (1) above in the emulsifying tank, and mixed. Upon completion of emulsification, the mixture was cooled to 40° C., and consecutively added with mixtures C and D which are prepared separately.
(4) Cooling was suspended when the temperature 30° C. and the product was taken off.

EXAMPLE 3

Eye-Liner (liquid type)

Using the materials listed in Table 4, an eye-liner product (liquid type) was prepared according to the following process.
(1) A was charged into the emulsifying tank and uniformly mixed while maintaining the temperature between 50° and 60° C.
(2) B was charged separately into the dissolving tank and heated to 50°–60° C.
(3) The mixture was added (2) to the mixture (1), emulsified and mixed. Upon completion of emulsification, the mixture was cooled to 40° C., consecutively added with the mixtures C and D prepared separately.
(4) Cooling was suspended when the temperature reached 30° C., and the product was taken off.

(2) C was then added to the pigment dispersed solution, agitated and mixed at a medium speed to obtain a uniform slurry. The viscosity at this stage is about 2000 cp by a rotary viscometer.
(3) The slurry was charged (dispersion solution) into the receiving vessel. A plurality of grindable resin pipes with the inner diameter of 6 φmm outer diameter of 10 φmm and length of 90 mm were set on the piston member (portion to be filled). The piston member was pressed into said receiving vessel and filled with the mixture by the action of backward flow.
(4) The apparatus was left standing with the piston member pressed (inserted) for 60 minutes at room temperature, dried together with the mold for 72 hours at 60° C. (RH 50%) and thoroughly hardened. The product thus obtained was a pencil-type cosmetic molded integrally with the mold without releasing the product from the molding pipe. The molding pipe is to be shaved at the time of use.

EXAMPLE 5

Stick Foundation

Using the materials listed in Table 5, a stick foundation was prepared according to the following process.
(1) A was charged into the dispersion tank, and the pigment was thoroughly dispersed by rotating the agitator at a high speed to obtain a dispersion solution.
(2) B was added to the pigment dispersed solution, further dispersed by rotating the agitator at a high speed, added with C by agitating at a medium speed to obtain a uniform slurry. The visocity at this stage was about 3000 cp by a rotary viscometer.
(3) The slurry (2) was pound into the metal mold with a bottom and having a plurality of tubular cavities having the opening diameter of 20 φmm and the

TABLE 4

| Liquid | Example 1 | | Example 2 | | Example 3 | |
|---|---|---|---|---|---|---|
| A | antiseptic | 0.1 | Carbopol 940 | 0.3 | Carbopol 940 | 0.3 |
| | triethanol amine | 2.0 | propyrene glycol | 2.5 | propylene glycol | 1.5 |
| | (coated pigments of preparation example 9) | 40.6 | coated pigments of preparation example 2 | 60.0 | coated pigments of preparation example 3 | 54.8 |
| | | | purified water | 20 | purified water | 32.95 |
| | polyethylene glycol | 12.0 | | | | |
| | purified water | 20.6 | | | | |
| B | liquid paraffin | 5.0 | liquid paraffin | 4.0 | liquid paraffin | 2.0 |
| | Bee's wax | 1.0 | surfactant | 0.08 | surfactant | 0.05 |
| | Setanol | 2.8 | | | | |
| | Lanolin | 2.0 | | | | |
| | Surfactant | 3.0 | | | | |
| | Stearic acid | 1.5 | | | | |
| C | perfume | 0.1 | antiseptic | 0.1 | ethanol | 2.0 |
| | | | ethanol | 5.0 | antiseptic | 0.1 |
| | | | perfume | 0.1 | perfume | 0.1 |
| D | | | triethanol amine | 0.3 | triethanol amine | 0.3 |
| | | | water | 7.62 | water | 6.0 |

EXAMPLE 4

Stick Eye-Shadow

Using the materials listed in Table 5, an eye-shadow stick was prepared according to the following process.
(1) A and B were charged into the dispersion tank, and A was dispersed by rotating the agitator at a high speed to obtain a dispersion solution containing the pigment.

length of 30 mm (by slanting the dispersion tank to directly pour the solution into the cavities).
(4) Upon completion of filling, the mixture was left standing for 2 hours at room temperature. The mixture was then dried together with the mold for 48 hours at 50° C. (RH 60%) and the thoroughly hardened product was removed.

EXAMPLE 6

Stick Rouge

Using the materials listed in Table 5, a stick rouge was prepared according to the following process.

(1) A was charged into the dispersion tank, and the coated pigment was dispersed thoroughly by rotating the agitator at a high speed to obtain a dispersion solution containing the pigment.

(2) B was added to the pigment dispersed solution, further dispersed by rotating the agitator at a medium speed to obtain a uniform slurry. The viscosity at this stage was about 1800 cp by a rotary viscometer.

(3) The slurry was charged to the receiving vessel, and a piston member having a plurality of through-holes (diameter of 9 $\phi$mm, length of 35 mm) was inserted into said vessel to fill the through-holes with the slurry by the action of backward flow.

(4) After inserting the piston member, the system was left standing for 60 minutes at room temperature. The system was dried together with the mold at 40° C. for 48 hours. When thoroughly hardened, the product was removed.

TABLE 5

| | Example 4 | | | Example 5 | | | Example 6 | | |
|---|---|---|---|---|---|---|---|---|---|
| A | Coated pigments of preparation example 4 | 30 | (60) | Coated pigments of preparation example 5 | 22.3 | (58) | Coated pigments of preparation example 6 | 24 | (47) |
| | | | | Water | 32.2 | (0) | purified water | 38 | |
| | | | | Glycerine | 0.5 | (2) | | | |
| B | Water | 25 | (0) | Squalane | 1.0 | (4) | Squalane | 1 | (4) |
| C | Gypsum | 10 | (40) | Gypsum | 9.0 | (36) | Gypsum | 12 | (48) |

What we claim is:

1. A coated pigment composition readily dispersed in water comprising at least one coated pigment and at least 20% by weight of said composition of of water; said pigment selected from the group consisting of titanium dioxide-coated mica, colored titanium dioxide-coated mica and colored bismuth oxychloride, coated on the surfaces thereof with a water-repellent coating of a metallic soap of the formula $(RCCO)_nM$, wherein R is selected from straight chain, branched chain, saturated and unsaturated aliphatic hydrocarbon groups having more than 6 carbon atoms, M is selected from aluminum and zinc, and n is the valency of the metal, said surface coating being prepared by reacting in an aqueous medium an alkaline salt of an aliphatic acid radical $(RCOO)^-$ with a mineral acid metal salt where said metal is M as defined above in a theoretical equivalent ratio of 1:4 to 1:10 and said pigments, the ratio by weight of said pigment to said so-formed soap being in the ratio of 1:0.01 to 1:0.1.

2. The coated pigment as claimed in claim 1, wherein the water content thereof is in the range of 50±10% by weight.

3. The coated pigment as claimed in claim 1, wherein said metallic saop contains an aliphatic group having from 8 to 20 carbon atoms.

4. The coated pigment as claimed in claim 1, wherein said metallic soap is the salt M with at least one acid selected from the group consisting of stearic acid, isostearic acid, myristic acid, palmitic acid, lauric acid and oleic acid.

5. The coated pigment as claimed in claim 4, wherein said metallic soap comprises at least one soap selected from the group consisting of aluminum stearate, zinc stearate, zinc myristate, and aluminum oleate.

6. The coated pigment as claimed in claim 5, wherein said pigment is titanium dioxide-coated mica.

7. The coated pigment as claimed in claim 5, wherein said pigment is colored titanium dioxide-coated mica.

8. The coated pigment as claimed in claim 5, wherein said pigment is colored bismuth oxychloride.

9. The coated pigment as claimed in claim 1, wherein said aliphatic acid alkaline salt is selected from sodium and potassium salts of stearic acid, isostearic acid, myristic acid, palmitic acid, lauric acid and oleic acid.

10. The coated pigment as claimed in claim 1, wherein said mineral acid metal salt is selected from aluminum chloride, aluminum sulfate, aluminum potassium sulfate, zinc chloride and zinc sulphate.

11. The method of preparing the dispersed pigment according to claim 1 which comprises the steps of coating said pigment with said water-repellent soap by reacting, in an aqeuous medium containing said pigments dispersed therein, said alkaline salt of the aliphatic acid radical $(RCOO)^-$ with the mineral acid salt of said metal M in the theoretical equivalent ratio of 1:4 to 1:10 and in an amount to cause said water-repellent soap to form and coat the surfaces of said pigment in a weight ratio of said pigment to said metallic soap in the weight range 1:0.01 to 1:0.1.

* * * * *